:# (12) United States Patent
Baravetto et al.

(10) Patent No.: US 6,174,522 B1
(45) Date of Patent: *Jan. 16, 2001

(54) CONDITIONING SHAMPOO COMPOSITION

(75) Inventors: John Thomas Baravetto, Cincinnati; Elizabeth Murphy Schrader; Timothy Woodrow Coffindaffer, both of Loveland; Susan Marie Guskey, Montgomery, all of OH (US)

(73) Assignee: The Procter & Gamble Company, Cincinnati, OH (US)

(*) Notice: Under 35 U.S.C. 154(b), the term of this patent shall be extended for 0 days.

This patent is subject to a terminal disclaimer.

(21) Appl. No.: 09/377,660

(22) Filed: Aug. 19, 1999

Related U.S. Application Data

(63) Continuation of application No. 08/738,152, filed on Oct. 25, 1996, now Pat. No. 5,980,877.

(51) Int. Cl.$^7$ .................. A61K 7/06; A61K 7/50
(52) U.S. Cl. .................. 424/70.12; 424/70.1; 424/70.11; 424/70.21; 424/70.22; 424/70.27; 424/70.31; 514/846
(58) Field of Search .................. 424/70.1, 70.11, 424/70.12, 70.21, 70.22, 70.27, 70.31; 514/846

(56) References Cited

U.S. PATENT DOCUMENTS

| | | | |
|---|---|---|---|
| 2,826,551 | 3/1958 | Geen | 252/89 |
| 3,964,500 | 6/1976 | Drakoff | 132/7 |
| 4,364,837 | 12/1982 | Pader | 252/173 |
| 4,733,677 | 3/1988 | Gee et al. | 132/7 |
| 4,741,855 | 5/1988 | Grote et al. | 252/142 |
| 4,788,006 | 11/1988 | Bolich, Jr. et al. | 252/550 |
| 5,037,818 | 8/1991 | Sime | 514/183 |
| 5,085,857 | 2/1992 | Reid et al. | 424/70 |
| 5,169,622 | 12/1992 | Kopolow et al. | 424/47 |
| 5,186,928 | 2/1993 | Birtwistle | 424/70 |
| 5,246,694 | 9/1993 | Birthwistle | 424/70 |

FOREIGN PATENT DOCUMENTS

| | | | |
|---|---|---|---|
| 0 226 337 | 6/1987 | (EP) | A61K/7/48 |
| 0 268 982 | 6/1988 | (EP) | A61K/7/06 |
| 0 413 416 | 2/1991 | (EP) | A61K/7/06 |
| 0 413 417 | 2/1991 | (EP) | A61K/7/06 |
| 0 432 951 | 6/1991 | (EP) | A61K/7/075 |
| 0 468 703 | 1/1992 | (EP) | A61K/7/075 |
| 0 468 721 | 1/1992 | (EP) | A61K/7/075 |
| 0 529 883 | 3/1993 | (EP) | A61K/7/00 |
| 0 552 024 | 7/1993 | (EP) | A61K/7/06 |
| 0 560 516 | 9/1993 | (EP) | A61K/7/06 |
| 0 674 898 | 10/1995 | (EP) | A61K/7/075 |
| 849433 | 9/1960 | (GB) | . |
| 54-129135 | 10/1979 | (JP) | A61K/7/06 |
| 56-72095 | 6/1981 | (JP) | A61K/7/06 |
| WO 94/03151 | 2/1994 | (WO) | A61K/7/50 |
| WO 95/01152 | 1/1995 | (WO) | A61K/7/06 |
| 95/09599 * | 4/1995 | (WO) | . |
| WO 95/09599 | 4/1995 | (WO) | A61K/7/06 |
| WO 95/22311 | 8/1995 | (WO) | A61K/7/48 |
| WO 95/24180 | 9/1995 | (WO) | A61K/7/06 |

OTHER PUBLICATIONS

*Microemulsions and Related Systems*, Mourice Bourrell, Robert S. Schechter, Marcel Dekker, Inc., pp. 25–30.
*The Aqueous Phase Behavior of Surfactants*, Robert G. Laughlin, Academic Press, p. 471.
*Surfactant Systems Their Chemistry, Pharmacy and Biology*, D. Attwood, A.T. Florence, Chapman and Hall, pp. 519–520.

* cited by examiner

Primary Examiner—Thurman K. Page
Assistant Examiner—Brian K. Seidleck
(74) *Attorney, Agent, or Firm*—Andrew A Paul; Tara M. Rosnell

(57) ABSTRACT

Disclosed are aqueous conditioning shampoo compositions containing a surfactant component in a shampoo with a particulate insoluble, dispersed, nonvolatile conditioning agent having a dual particle size range, suspending agent and a deposition polymer.

22 Claims, No Drawings

CONDITIONING SHAMPOO COMPOSITION

The instant application is a continuation of U.S. Ser. No. 08/738,152, filed on Oct. 25, 1996 now U.S. Pat. No. 5,980,877, issued Nov. 9, 1999.

FIELD OF THE INVENTION

This invention relates to conditioning shampoo compositions containing a surfactant component in a shampoo with a particulate insoluble, dispersed, nonvolatile conditioning agent having a dual particle size range, suspending agent and a deposition polymer. The compositions provide improved hair conditioning performance, including improved wet hair feel.

BACKGROUND OF THE INVENTION

Human hair becomes soiled due to its contact with the surrounding atmosphere and, to a greater extent, from sebum secreted by the head. The build-up of the sebum causes the hair to have a dirty feel and an unattractive appearance. The soiling of the hair necessitates it being shampooed with frequent regularity.

Shampooing the hair cleans by removing excess soil and sebum. However, the shampooing process has disadvantages in that the hair is left in a wet, tangled and generally unmanageable state. Shampooing can also result in the hair becoming dry or "frizzy", and a loss of luster, due to removal of natural oils or other hair moisturizing materials. After shampooing, the hair can also suffer from a loss of "softness" perceived by the user upon drying. The hair can also suffer from increased levels of static upon drying after shampooing. This can interfere with combing and can result in fly-away hair. A variety of approaches have been developed to alleviate the after-shampoo problems. These range from the inclusion of hair conditioning aids in shampoos to post-shampoo application of hair conditioners, i.e., hair rinses. Hair rinses are generally liquid in nature and must be applied in a separate step following the shampooing, left on the hair for a length of time, and rinsed with fresh water. This, of course, is time consuming and is not as convenient as shampoos containing both cleaning and hair conditioning ingredients.

While a wide variety of shampoos have been disclosed which contain conditioning aids, they have not been totally satisfactory for a variety of reasons. Cationic conditioning agents are highly desirable for use in hair conditioning due to their abilities to control static, improve wet detangling, and provide a silky wet hair feel to the user. One problem which has been encountered in shampoos relates to compatibility problems between good cleaning anionic surfactants and the many conventional cationic agents which historically have been used as conditioning agents. Efforts have been made to minimize adverse interaction through the use of alternate surfactants and improved cationic conditioning agents. Cationic surfactants which provide good overall conditioning in hair rinse products, in general, tend to complex with anionic cleaning surfactants and provide poor conditioning in a shampoo context. In particular, the use of soluble cationic surfactants that form soluble ionic complexes do not deposit well on the hair. Soluble cationic surfactants that form insoluble ionic complexes deposit on the hair but do not provide good hair conditioning benefits, and tend to cause the hair to have a dirty, coated feel. The use of insoluble cationic surfactants, e.g., tricetyl methyl ammonium chloride, can provide excellent anti-static benefits but do not otherwise provide good overall conditioning.

Many cationic polymers tend to build up on the hair to result in an undesirable, "unclean" coated feel. Cationic polymers therefore, conventionally, are preferably used at limited levels to minimize this problem. This, however, can limit the overall conditioning benefits that are obtained. Additionally, cationic conditioning agents commonly do not provide optimal overall conditioning benefits, particularly in the area of "softness", especially when delivered as an ingredient in a shampoo composition.

Materials which can provide increased softness are non-ionic silicones. Silicones in shampoo compositions have been disclosed in a number of different publications. Such publications include U.S. Pat. No. 2,826,551, Geen, issued Mar. 11, 1958; U.S. Pat. No. 3,964,500, Drakoff, issued Jun. 22, 1976; U.S. Pat. No. 4,364,837, Pader, issued Dec. 21, 1982; and British Patent 849,433, Woolston, issued Sep. 28, 1960. While these patents disclose silicone containing compositions, they also did not provide a totally satisfactory product in that it was difficult to maintain the silicone well dispersed and suspended in the product. Recently, stable, insoluble silicone-containing hair conditioning shampoo compositions have been described in U.S. Pat. No. 4,741,855, Grote and Russell, issued May 3, 1988 and U.S. Pat. No. 4,788,066, Bolich and Williams, issued Nov. 29, 1988. These shampoo compositions can deliver excellent overall conditioning benefits to the hair while maintaining excellent cleaning performance, even with the use of anionic detersive surfactants, for a wide variety of hair types.

More recently, improved conditioning shampoos were provided in U.S. Ser. No. 07/622,699, Robert L. Wells, filed Dec. 5, 1990, now abandoned, and its continuation application Ser. No. 07/778,765, filed Oct. 21, 1991 now abandoned, wherein shampoos containing anionic surfactant, dispersed, insoluble silicone, and certain relatively low ionic strength cationic polymers (greater than about 0.4 meq./gm) were disclosed. These compositions provide excellent hair cleaning conditioning to a wide variety of hair types, especially including improved conditioning to hair damaged by color treatments, bleaching, permanents, etc.

Japanese Patent Application, Laid Open No. 56-72095, Jun. 16, 1981, Hirota et al. (Kao Soap Corp.) also discloses shampoo containing cationic polymer and silicone conditioning agents. Still other patent publications relating to shampoos with cationic agents and silicone include EPO Application Publication 0 413 417, published Feb. 20, 1991, Hartnett et al.

Another approach to providing hair conditioning benefits to shampoo compositions has been to use materials which are oily to the touch. These materials provide improved luster and shine to the hair. Oily materials have also been combined with cationic materials in the shampoo formulations. Japanese Patent Application Showa 53-35902, laid open Oct. 6, 1979 (Showa 54-129135), N. Uchino (Lion Yushi Co.), discloses hair treatment compositions containing cationic polymer, fatty acid salt, and at least 10% of an oily component for use before or after shampooing. Suitable oily components are hydrocarbons, higher alcohols, fatty acid esters, glycerides, and fatty acids. Japanese Patent Application 62 [1987]-327266, filed Dec. 25, 1987, published Jul. 4, 1989, laid open No. HEI 1 [19871]-168612, Horie et al., discloses detergent compositions containing cationic surfactant and/or cationic polymer, anionic surfactant, and specific esters of the formula RCOOR' wherein R and R' are straight or branched chain alkyls.

In spite of these attempts to provide optimal combinations of cleaning ability and hair conditioning, it remains desirable to provide further improved hair conditioning shampoo compositions. For instance, it remains desirable to improve overall conditioning, and especially shine and luster, wet and dry combing, and dry hair feel, of hair treated with shampoo containing silicone and cationic material. For shampoos containing oily materials in combination with cationic materials, it remains desirable to improve overall conditioning, especially wet combing and detangling, dry combing, and dry hair feel. However merely increasing the level of one or both conditioning ingredients can result in adverse effects such as greasy hair feel and loss of fullness. It is desirable to improve conditioning without suffering from these drawbacks.

One attempt to do this is disclosed in EPO Patent Publication No. 0413 416, published Feb. 20, 1991, Robbins et al., which discloses shampoo containing aminosilicone, anionic surfactant, cationic surfactant, and a hydrocarbon component. These types of formulations would normally be expected to result in either excessive buildup of aminosilicone on the hair, and consequently greasy hair feel and loss of fullness, or a relatively limited degree of improvement due to intentional use of very low levels of aminosilicone to avoid such adverse effects. The cationic surfactants would have limited ability to condition the hair due to interaction with the anionic surfactant.

EPO Patent Application Publication No. 0 413 417, published Feb. 20, 1991, discloses shampoo containing anionic surfactant, and conditioning agents such as insoluble silicone (preferably aminosilicone), cationic surfactant, polyethylenes, paraffins, microcrystalline waxes, $C_{18}$–$C_{36}$ fatty acids or triglycerides, high fatty alcohol esters of high fatty acids, and beeswax. Another patent document which discloses shampoo compositions and a variety of conditioning agents is U.S. Pat. No. 3,964,500, Drakoff, issued Jun. 22, 1976. This patent relates to shampoo containing silicone conditioner and a hair bodying agent selected from certain wood rosins, shellac, sucrose acetate isobutyrate, and cationic amino cellulose.

A recent approach to providing hair conditioning benefits to shampoo is described in U.S. Pat. No. 5,085,857 (Reid et al.). The composition disclosed combines a surfactant system (selected from anionic, nonionic, or amphoteric, or mixtures thereof), cationic guar derived polymer, and non-volatile silicone having particle size less than 2 microns.

In spite of all these approaches and attempts to provide optimum combinations of shampoos and hair conditioners, it remains desirable to provide still improved conditioning shampoos. It has now been found that improved overall conditioning, especially wet conditioning, can be achieved by combining a surfactant component in a shampoo with a particulate insoluble, dispersed, nonvolatile conditioning agent having a dual particle size range, suspending agent and a deposition polymer. These compositions can provide improved conditioning while reducing the level of undesirable side effects that can result from increasing the level of conditioning agent in prior known conditioning systems. As discussed previously, a conditioning agent system containing too much silicone can result in silicone build up on the hair over repeated usages and to loss of fullness of the hair. Too much oil results in an oily feel and a loss of fullness of the hair. Too much cationic conditioning agent results in a coated, dirty feel of the hair. Now it has been found that the components of the present invention can provide improved overall conditioning while minimizing the adverse effects of conditioning agent build-up that otherwise can be incurred upon increasing the levels of individual components in prior known conditioning systems.

It is an object of this invention to provide shampoo compositions, which can provide excellent cleaning performance and improved levels of conditioning while minimizing any adverse side effects associated with build-up due to the use of excess conditioning agent.

It is also an object of this invention to provide a method for cleaning and conditioning the hair which can provide excellent cleaning in combination with improved conditioning, while minimizing adverse side effects associated with excess build-up of conditioning agent on the hair.

These objects will become apparent from the description which follows, as may other objects become apparent upon a reading of said description.

SUMMARY OF THE INVENTION

An aqueous shampoo composition comprising:
a) from about 5.0% to about 50% of a surfactant component,
b) a conditioning component comprising:
  i) a first non-volatile conditioning agent having a mean particle size of less than about 2 microns; and
  ii) a second non-volatile conditioning agent having a mean particle size of greater than about 5 microns;
c) from about 0.01% to about 3.0% of a deposition polymer;
d) from about 0.1% to about 5% of a suspending agent; and
e) an aqueous carrier.

DETAILED DESCRIPTION OF THE INVENTION

The shampoo compositions of the present invention can comprise, consist of, or consist essentially of the essential elements and limitations of the invention described herein, as well any of the additional or optional ingredients, components, or limitations described herein.

All percentages, parts and ratios are based upon the total weight of the shampoo compositions of the present invention, unless otherwise specified. All such weights as they pertain to listed ingredients are based on the active level and, therefore, do not include carriers or by-products that may be included in commercially available materials, unless otherwise specified.

As used herein, the term "soluble" refers to any material that is sufficiently soluble in water to form a substantially clear solution to the naked eye at a concentration of 0.1% by weight of the material in water at 25° C. Conversely, the term "insoluble" refers to all other materials that are therefore not sufficiently soluble in water to form a substantially clear solution to the naked eye at a concentration of 0.1% by weight of the other material in water at 25° C.

As used herein, the term "liquid" refers to any visibly (by the naked eye) flowable fluid under ambient conditions (about 1 atmosphere of pressure at about 25° C.).

The shampoo compositions of the present invention, including the essential and optional components thereof, are described in detail hereinafter.

Surfactant Component

Detersive Surfactant

The shampoo compositions of the present invention comprise a detersive surfactant suitable for use on hair or skin. Suitable surfactants include anionic surfactants, nonionic surfactants, amphoteric surfactants, zwitterionic surfactants, or mixtures thereof. The purpose of the detersive surfactant is to provide cleansing performance to the composition. The term detersive surfactant, as used herein, is intended to distinguish these surfactants from surfactants which are primarily emulsifying surfactants, i.e. surfactants which provide an emulsifying benefit and which have low cleansing performance. It is recognized that most surfactants have both detersive and emulsifying properties. It is not intended to exclude emulsifying surfactants from the present invention, provided the surfactant also possesses sufficient detersive properties to be useful herein.

Concentrations of the surfactant in the shampoo composition range from about 5% to about 50%, preferably from about 8% to about 30%, and more preferably from about 10% to about 25%, by weight of the composition.

Anionic Surfactants

Anionic surfactants useful herein include alkyl and alkyl ether sulfates. These materials have the respective formulae $ROSO_3M$ and $RO(C_2H_4O)_xSO_3M$, wherein R is alkyl or alkenyl of from about 8 to about 30 carbon atoms, x is 1 to about 10, and M is hydrogen or a cation such as ammonium, alkanolammonium (e.g., triethanolammonium), a monovalent metal cation (e.g., sodium and potassium), or a polyvalent metal cation (e.g., magnesium and calcium). Preferably, M should be chosen such that the anionic surfactant component is water soluble. The anionic surfactant or surfactants should be chosen such that the Krafft temperature is about 15° C. or less, preferably about 10° C. or less, and more preferably about 0° or less. It is also preferred that the anionic surfactant be soluble in the composition hereof.

Krafft temperature refers to the point at which solubility of an ionic surfactant becomes determined by crystal lattice energy and heat of hydration, and corresponds to a point at which solubility undergoes a sharp, discontinuous increase with increasing temperature. Each type of surfactant will have its own characteristic Krafft temperature. Krafft temperature for ionic surfactants is, in general, well known and understood in the art. See, for example, Myers, Drew, *Surfactant Science and Technology*, pp. 82–85, VCH Publishers, Inc. (New York, N.Y., USA), 1988 (ISBN 0-89573-399-0), which is incorporated by reference herein in its entirety.

In the alkyl and alkyl ether sulfates described above, preferably R has from about 12 to about 18 carbon atoms in both the alkyl and alkyl ether sulfates. The alkyl ether sulfates are typically made as condensation products of ethylene oxide and monohydric alcohols having from about 8 to about 24 carbon atoms. The alcohols can be derived from fats, e.g., coconut oil, palm oil, tallow, or the like, or the alcohols can be synthetic. Lauryl alcohol and straight chain alcohols derived from coconut oil and palm oil are preferred herein. Such alcohols are reacted with 1 to about 10, and especially about 3, molar proportions of ethylene oxide and the resulting mixture of molecular species having, for example, an average of 3 moles of ethylene oxide per mole of alcohol, is sulfated and neutralized.

Specific examples of alkyl ether sulfates which can be used in the present invention are sodium and ammonium salts of coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 12 to about 16 carbon atoms and an average degree of ethoxylation of from 1 to about 4 moles of ethylene oxide. Such a mixture also comprises from 0% to about 20% by weight of $C_{12-13}$ compounds; from about 60% to about 100% by weight of $C_{14-15-16}$ compounds, from 0% to about 20% by weight of $C_{17-18-19}$ compounds; from about 3% to about 30% by weight of compounds having a degree of ethoxylation of 0; from about 45% to about 90% by weight of compounds having a degree of ethoxylation of from 1 to about 4; from about 10% to about 25% by weight of compounds having a degree of ethoxylation of from about 4 to about 8; and from about 0.1% to about 15% by weight of compounds having a degree of ethoxylation greater than about 8.

Other suitable anionic surfactants are the water-soluble salts of organic, sulfuric acid reaction products of the general formula $[R_1-SO_3-M]$ where $R_1$ is selected from the group consisting of a straight or branched chain, saturated aliphatic hydrocarbon radical having from about 8 to about 24, preferably about 10 to about 18, carbon atoms; and M is as previously described above in this section. Examples of such surfactants are the salts of an organic sulfuric acid reaction product of a hydrocarbon of the methane series, including iso-, neo-, and n-paraffins, having about 8 to about 24 carbon atoms, preferably about 12 to about 18 carbon atoms and a sulfonating agent, e.g., $SO_3$, $H_2SO_4$, obtained according to known sulfonation methods, including bleaching and hydrolysis. Preferred are alkali metal and ammonium sulfonated $C_{10-18}$ n-paraffins.

Still other suitable anionic surfactants are the reaction products of fatty acids esterified with isethionic acid and neutralized with sodium hydroxide where, for example, the fatty acids are derived from coconut or palm oil; or sodium or potassium salts of fatty acid amides of methyl tauride in which the fatty acids, for example, are derived from coconut oil. Other similar anionic surfactants are described in U.S. Pat. Nos. 2,486,921, 2,486,922, and 2,396,278, which are incorporated by reference herein in their entirety.

Other anionic surfactants suitable for use in the shampoo compositions are the succinates, examples of which include disodium N-octadecylsulfosuccinate; disodium lauryl sulfosuccinate; diammonium lauryl sulfosuccinate; tetra sodium N-(1,2-dicarboxyethyl)-N-octadecylsulfosuccinate; the diamyl ester of sodium sulfosuccinic acid; the dihexyl ester of sodium sulfosuccinic acid; and the dioctyl ester of sodium sulfosuccinic acid.

Other anionic surfactants suitable for use in the shampoo compositions are those that are derived from amino acids. Nonlimiting examples of such surfactants include N-acyl-L-glutamate, N-acyl-N-methyl-p-alanate, N-acylsarcosinate, and their salts.

Still other useful surfactants are those that are derived from taurine, which is also known as 2-aminoethanesulfonic acid. An example of such an acid is N-acyl-N-methyl taurate.

Other suitable anionic surfactants include olefin sulfonates having about 10 to about 24 carbon atoms. The term "olefin sulfonates" is used herein to mean compounds which can be produced by the sulfonation of alpha-olefins by means of uncomplexed sulfur trioxide, followed by neutralization of the acid reaction mixture in conditions such that any sulfones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form.

The alpha-olefins from which the olefin sulfonates are derived are mono-olefins having about 12 to about 24 carbon atoms, preferably about 14 to about 16 carbon atoms. Preferably, they are straight chain olefins.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process. A specific alpha-olefin sulfonate mixture of the above type is described more fully in U.S. Pat. No. 3,332,880, to Pflaumer and Kessler, issued Jul. 25, 1967, which is incorporated by reference herein in its entirety.

Another class of anionic surfactants suitable for use in the shampoo compositions are the beta-alkyloxy alkane sulfonates. These compounds have the following formula:

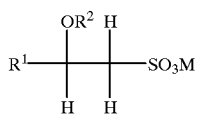

where $R^1$ is a straight chain alkyl group having from about 6 to about 20 carbon atoms, $R^2$ is a lower alkyl group having from about 1, preferred, to about 3 carbon atoms, and M is as hereinbefore described. Many other anionic surfactants suitable for use in the shampoo compositions are described in *McCutcheon's, Emulsifiers and Detergents* 1989 *Annul*, published by M. C. Publishing Co., and in U.S. Pat. No. 3,929,678, which descriptions are incorporated herein by reference in their entirety. Preferred anionic surfactants for use in the shampoo compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamnine lauyl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lawyl sulfate, monoethanolamine cocoyl sulfate, monoethanolamine lauryl sulfate, sodium tridecyl benzene sulfonate, and sodium dodecyl benzene sulfonate, sodium N-lauroyl-L-glutamate, triethanol N-lauryoyl-L-glutamate, sodium N-lauroyl-N-methyl taurate, sodium N-lauroyl-N-methyl-β-aminopropionate, and mixtures thereof.

Amphoteric and Zwitterionic Surfactants

The shampoo compositions can comprise amphoteric and/or zwitterionic surfactants. Amphoteric surfactants suitable for use in the shampoo compositions include the derivatives of aliphatic secondary and tertiary amines in which the aliphatic radical is straight or branched and one of the aliphatic substituents contains from about 8 to about 18 carbon atoms and one contains an anionic water solubilizing group, e.g., carboxy, sulfonate, sulfate, phosphate, or phosphonate.

Zwitterionic surfactants suitable for use in the shampoo compositions include the derivatives of aliphatic quaternary ammonium, phosphonium, and sulfonium compounds, in which the aliphatic radicals are straight or branched, and wherein one of the aliphatic substituents contains from about 8 to about 18 carbon atoms and one contains an anionic group, e.g., carboxy, sulfonate, sulfate, phosphate, or phosphonate. A general formula for these compounds is:

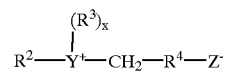

where $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing 1 to about 3 carbon atoms; X is 1 when Y is a sulfur atom, and 2 when Y is a nitrogen or phosphorus atom; $R^4$ is an alkylene or hydroxyalkylene of from 1 to about 4 carbon atoms and Z is a radical selected from the group consisting of carboxylate, sulfonate, sulfate, phosphonate, and phosphate groups.

Examples of amphoteric and zwitterionic surfactants also include sultaines and amidosultaines. Sultaines, including amidosultaines, include for example, cocodimethylpropylsultaine, stearyldimethylpropylsultaine, lauryl-bis-(2-hydroxyethyl) propylsultaine and the like; and the amidosultaines such as cocamidodimethylpropylsultaine, stearylamridododimethylpropylsultaine, laurylamidobis-(2-hydroxyethyl) propylsultaine, and the like. Preferred are amidohydroxysultaines such as the $C_{12}$–$C_{18}$ hydrocarbyl amidopropyl hydroxysultaines, especially $C_{12}$–$C_{14}$ hydrocarbyl amido propyl hydroxysultaines, e.g., laurylamidopropyl hydroxysultaine and cocamidopropyl hydroxysultaine. Other sultaines are described in U.S. Pat. No. 3,950,417, which is incorporated herein by reference in its entirety.

Other suitable amphoteric surfactants are the aminoalkanoates of the formula R—NH(CH$_2$)$_2$COOM, the iminodialkanoates of the formula R—N[(CH$_2$)$_m$COOM]$_2$ and mixtures thereof; wherein n and m are numbers from 1 to about 4, R is $C_8$–$C_{22}$ alkyl or alkenyl, and M is hydrogen, alkali metal, alkaline earth metal, ammonium or alkanolammonium.

Examples of suitable aminoalkanoates include n-alkylamino-propionates and n-alkyliminodipropionates, specific examples of which include N-lauryl-beta-amino propionic acid or salts thereof, and N-lauryl-beta-iminodipropionic acid or salts thereof, and mixtures thereof.

Other suitable amphoteric surfactants include those represented by the formula:

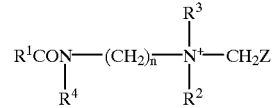

wherein $R^1$ is $C_8$–$C_{22}$ alkyl or alkenyl, preferably $C_{12}$–$C_{16}$, $R^2$ and $R^3$ is independently selected from the group consisting of hydrogen, CH$_2$CO$_2$M, CH$_2$CH$_2$OH, CH$_2$CH$_2$CH$_2$OCH$_2$CH$_2$COOM, or (CH$_2$CH$_2$O)$_m$H wherein m is an integer from 1 to about 25, and $R^4$ is hydrogen, CH$_2$CH$_2$OH, or CH$_2$CH$_2$OCH$_2$CH$_2$COOM, Z is CO$_2$M or CH$_2$CO$_2$M, n is 2 or 3, preferably 2, M is cation, such as alkali metal (e.g., lithium, sodium, potassium), alkaline earth metal (beryllium, magnesium, calcium, strontium, barium), or ammonium. This type of surfactant is sometimes classified as an imidazoline-type amphoteric surfactant, although it should be recognized that it does not necessarily have to be derived, directly or indirectly, through an imidazoline intermediate. Suitable materials of this type are marketed under the tradename MIRANOL and are understood to comprise a complex mixture of species, and can exist in protonated and non-protonated species depending upon pH with respect to species that can have a hydrogen at $R^2$. All such variations and species are meant to be encompassed by the above formula.

Examples of surfactants of the above formula are monocarboxylates and dicarboxylates. Examples of these materials include cocoamphocarboxypropionate, cocoamphocarboxypropionic acid, cocoamphocarboxyglycinate (alternately referred to as cocoamphodiacetate), and cocoamphoacetate.

Commercial amphoteric surfactants include those sold under the trade names MIRANOL C2M CONC. N. P., MIRANOL C2M CONC. O. P., MIRANOL C2M SF, MIRANOL CM SPECIAL (Miranol, Inc.); ALKATERIC 2CIB (Alkaril Chemicals); AMPHOTERGE W-2 (Lonza, Inc.); MONATERIC CDX-38, MONATERIC CSH-32 (Mona Industries); REWOTERIC AM-2C (Rewo Chemical Group); and SCHERCOTERIC MS-2 (Scher Chemicals).

Betaine surfactants, i.e. zwitterionic surfactants, suitable for use in the shampoo compositions are those represented by the formula:

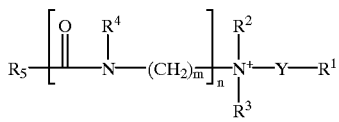

wherein:

$R^1$ is a member selected from the group consisting of

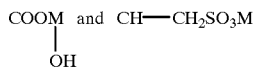

$R_2$ is lower alkyl or hydroxyalkyl;
$R_3$ is lower alkyl or hydroxyalkyl;
$R_4$ is a member selected from the group consisting of hydrogen and lower alkyl;
$R_5$ is higher alkyl or alkenyl;
Y is lower alkyl, preferably methyl;
m is an integer from 2 to 7, preferably from 2 to 3;
n is the integer 1 or 0;
M is hydrogen or a cation, as previously described, such as an alkali metal, alkaline earth metal, or ammonium. The term "lower alkyl" or "hydroxyalkyl" means straight or branch chained, saturated, aliphatic hydrocarbon radicals and substituted hydrocarbon radicals having from one to about three carbon atoms such as, for example, methyl, ethyl, propyl, isopropyl, hydroxypropyl, hydroxyethyl, and the like. The term "higher alkyl or alkenyl" means straight or branch chained saturated (i.e., "higher alkyl") and unsaturated (i.e., "higher alkenyl") aliphatic hydrocarbon radicals having from about eight to about 20 carbon atoms such as, for example, lauryl, cetyl, stearyl, oleyl, and the like. It should be understood that the term "higher alkyl or alkenyl" includes mixtures of radicals which may contain one or more intermediate linkages such as ether or polyether linkages or non-functional substituents such as hydroxyl or halogen radicals wherein the radical remains of hydrophobic character.

Examples of surfactant betaines of the above formula wherein n is zero which are useful herein include the alkylbetaines such as cocodimethylcarboxymethylbetaine, lauryldimethylcarboxymethylbetaine, lauryl dimethyl-alpha-carboxyethylbetaine, cetyldimethylcarboxymethylbetaine, lauryl-bis-(2-hydroxyethyl) carboxymethylbetaine, stearyl-bis-(2-hydroxypropyl) carboxymethylbetaine, oleyldimethyl-gamma-carboxypropylbetaine, lauryl-bix-(2-hydroxypropyl)alpha-carboxyethylbetaine, etc. The sulfobetaines may be represented by cocodimethylsulfopropylbetaine, stearyldimethylsulfopropylbetaine, lauryl-bis-(2-hydroxyethyl)sulfopropylbetaine, and the like.

Specific examples of amido betaines and amidosulfo betaines useful in the shampoo compositions include the amidocarboxybetaines, such as cocamidodimethylcarboxymethylbetaine, laurylamidodimethylcarboxymethylbetaine, cetylamidodimethylcarboxymethylbetaine, laurylamido-bis-(2-hydroxyethyl)-carboxymethylbetaine, cocamido-bis-(2-bydroxyethyl)-carboxymethylbetaine, etc. The amido sulfobetaines may be represented by cocamidodimethylsulfopropylbetaine, stearylamidodimethylsulfopropylbetaine, laurylamidobis-(2-hydroxyethyl)sulfopropylbetaine, and the like.

Nonionic Surfactants

The shampoo compositions of the present invention can comprise a nonionic surfactant, suitable examples of which include those compounds produced by condensation of alkylene oxide groups, hydrophilic in nature, with an organic hydrophobic compound, which may be aliphatic or alkyl aromatic in nature.

Preferred nonlimiting examples of nonionic surfactants for use in the shampoo compositions include the following:

(1) polyethylene oxide condensates of alkyl phenols, e.g., the condensation products of alkyl phenols having an alkly group containing from about 6 to about 20 carbon atoms in either a straight chain or branched chain configuration, with ethylene oxide, the said ethylene oxide being present in amounts equal to from about 10 to about 60 moles of ethylene oxide per mole of alkyl phenol;

(2) those derived from the condensation of ethylene oxide with the product resulting from the reaction of propylene oxide and ethylene diamine products;

(3) long chain tertiary amine oxides of the formula $[R^1R^2R^3N \rightarrow O]$ where $R^1$ contains an alkyl, alkenyl or monohydroxy alkyl radical of from about 8 to about 18 carbon atoms, from 0 to about 10 ethylene oxide moieties, and from 0 to about 1 glyceryl moiety, and $R^2$ and $R^3$ contain from about 1 to about 3 carbon atoms and from 0 to about 1 hydroxy group, e.g., methyl, ethyl, propyl, hydroxyethyl, or hydroxypropyl radicals;

(4) long chain tertiary phosphine oxides of the formula $[RR'R"P \rightarrow O]$ where R contains an alkyl, alkenyl or monohydroxyalkyl radical ranging from about 8 to about 18 carbon atoms in chain length, from 0 to about 10 ethylene oxide moieties and from 0 to 1 glyceryl moieties and R' and R" are each alkyl or monohydroxyalkyl groups containing from about 1 to about 3 carbon atoms;

(5) long chain dialkyl sulfoxides containing one short chain alkyl or hydroxy alkyl radical of from 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to 1 glyceryl moieties; and (6) alkyl polysaccharide (APS) surfactants (e.g. alkyl polyglycosides), examples of which are described in U.S. Pat. No. 4,565,647, which is incorporated herein by reference in its entirety, and which discloses APS surfactants having a hydrophobic group with about 6 to about 30 carbon atoms and a polysaccharide (e.g., polyglycoside) as the hydrophilic group; optionally, there can be a polyalkylene-oxide group joining the hydrophobic and hydrophilic moieties; and the alkyl group (i.e., the hydrophobic moiety) can be saturated or unsaturated, branched or unbranched, and unsubstituted or substituted (e.g., with hydroxy or cyclic rings); a preferred material is alkyl polyglucoside which is commercially available from Henkel, ICI Americas, and Seppic.

The preferred shampoo compositions of the present invention comprise from about 5.0% to about 50% of a detersive surfactant component comprising: i) an ethoxylated alkyl sulfate surfactant having from about 1 to about 8 moles of ethoxylation; and ii) an amphoteric surfactant component to provide cleaning performance to the composition and wherein said the resulting composition comprises less than about 5%, preferably less than about 3% and most preferably less than about 2% of alkyl sulfate ethoxylated surfactant having less than 1 mole of ethoxylation.

Insoluble Hair Conditioning Component

The shampoo compositions of the present invention further comprises an insoluble hair conditioning component comprising:
 i) a first non-volatile conditioning agent having a mean particle size of less than about 2 microns; and
 ii) a second non-volatile conditioning agent having a mean particle size of greater than about 5 microns.

The hair conditioning component is used at concentrations effective to provide hair conditioning benefits. Such concentrations generally range from about 0.005% to about 10%, preferably from about 0.05% to about 5%, more preferably from about 0.1% to about 4%, most preferably from about 0.2% to about 3%, by weight of the shampoo compositions. The first non-volatile conditioning agent in the present invention (the smaller particles) have a mean particle size range below about 2 microns, preferably below about 1 micron, more preferably below about 0.5 microns, even more preferably below about 0.3 microns, even more preferably below about 0.15 microns, and most preferably below about 0.05 microns, and preferably greater than about 0.01 microns. The second non-volatile conditioning agent in the present invention (the larger particles) have a mean particle size range greater than about 5 microns, preferably from about 5 microns to about 500 microns, more preferably from about 10 microns to about 200 microns more preferably from about 15 microns to about 100 microns and most preferably from about 20 microns to about 75 microns. The first and second non-volatile conditioning agents are used in a ratio of from about 1 to 10 to about 10 to 1, preferably from about 5 to 1 to about 1 to 5 and most preferably from about 3 to 1 to about 1 to 3.

As used herein, average particle size of the conditioning agent particles may be measured within the shampoo compositions by light scattering methods well known in the art for determining average particle size for emulsified liquids. One such method involves the use of a Horiba LA-910 particle size analyzer.

The smaller particle size range materials can be formed by mechanical emulsification or by emulsion polymerization, both means are well-known in the art, see, for example, U.S.

Pat. No. 4,733,677, issued Mar. 29, 1988 to Gee et al., and U.S. Pat No. 5,085,857 issued Feb. 4, 1992 to Reid et al. and WO 95/09599, published Apr. 13, 1995 to Murray, all of which are incorporated by reference herein.

The particles for the two components can be the same material, different materials, or mixtures of different materials as described below. Useful conditioning agents for the two components include, but are not limited to non-volatile silicone conditioning agents, hydrocarbon oils, fatty ester oils and petrolatum, preferably silicone and are described in detail below.

Silicone Hair Conditioning Agent

Most preferred for use herein are non-volatile silicone conditioning agents. Typically it will be intermixed in the shampoo composition so as to be in the form of a separate, discontinuous phase of dispersed, insoluble particles, also referred to as droplets. These droplets may be suspended with a suspending agent described hereinafter. The silicone hair conditioning agent phase will comprise a silicone fluid hair conditioning agent such as a silicone fluid and can also comprise other ingredients, such as silicone gums and resins to enhance silicone fluid deposition efficiency or enhance glossiness of the hair (especially when high refractive index (e.g. above about 1.46) silicone conditioning agents are used (e.g. highly phenylated silicones).

As used herein, "nonvolatile" refers to silicone material with little or no significant vapor pressure under ambient conditions, as is understood by those in the art. Boiling point under one atmosphere (atm) will preferably be at least about 250° C., more preferably at least about 275° C., most preferably at least about 300° C. Vapor pressure is preferably about 0.2mm HG at 25° C. or less, preferably about 0.1 mm HG at 25° C. or less.

The silicone hair conditioning agent phase may comprise volatile silicone, nonvolatile silicone, or mixtures thereof. Typically, if volatile silicones are present, it will be incidental to their use as a solvent or carrier for commercially available forms of nonvolatile silicone materials ingredients, such as silicone gums and resins.

The silicone hair conditioning agents for use in the shampoo compositions preferably have a viscosity of from about 20 to about 2,000,000 centistokes, more preferably from about 1,000 to about 1,800,000 centistokes, even more preferably from about 10,000 to about 1,500,000 centistokes, most preferably from about 30,000 to about 1,000,000 centistokes, at 25° C. The viscosity can be measured by means of a glass capillary viscometer as set forth in Dow Coming Corporate Test Method CTM0004, Jul. 20, 1970.

Optional silicone fluid for use in the shampoo compositions includes silicone oil which are flowable silicone materials with a viscosity of less than 1,000,000 centistokes, preferably between about 5 and 1,000,000 centistokes, more preferably between about 10 and about 600,000 centistokes, more preferably between about 10 and about 500,000 centistokes, most preferably between 10 and 300,000 centistokes at 25° C. Suitable silicone oils include polyalkyl siloxanes, polyaryl siloxanes, polyalkylaryl siloxanes, polyether siloxane copolymers, and mixtures thereof. Other insoluble, nonvolatile silicone fluids having hair conditioning properties can also be used.

Optional Silicone oils for use in the composition include polyalkyl or polyaryl siloxanes which conform to following formula:

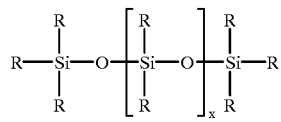

where R is aliphatic, preferably alkyl or alkenyl, or aryl, R can be substituted or unsubstituted, and x is an integer from 1 to about 8,000. Suitable unsubstituted R groups include alkoxy, aryloxy, alkaryl, arylalkyl, arylalkenyl, alkamino, and ether-substituted, hydroxyl-substituted, and halogen-substituted aliphatic and aryl groups. Suitable R groups also include cationic amines and quaternary ammonium groups.

The aliphatic or aryl groups substituted on the siloxane chain may have any structure as long as the resulting silicones remain fluid at room temperature, are hydrophobic, are neither irritating, toxic nor otherwise harmful when applied to the hair, are compatible with the other components of the shampoo compositions, are chemically stable under normal use and storage conditions, are insoluble in the shampoo compositions, and are capable of being deposited on and, of conditioning, the hair.

The two R groups on the silicon atom of each monomeric silicone unit may represent the same group or different groups. Preferably, the two R groups represent the same group.

Preferred alkyl and alkenyl substituents are $C_1$–$C_5$ alkyls and alkenyls, more preferably from $C_1$–$C_4$, most preferably from $C_1$–$C_2$. The aliphatic portions of other alkyl-, alkenyl-, or alkynyl-containing groups (such as alkoxy, alkaryl, and alkamino) can be straight or branched chains and preferably have from one to five carbon atoms, more preferably from one to four carbon atoms, even more preferably from one to three carbon atoms, most preferably from one to two carbon atoms. As discussed above, the R substituents hereof can also contain amino functionalities, e.g. alkamino groups, which can be primary, secondary or tertiary amines or quaternary ammonium. These include mono-, di- and tri-alkylamino and alkoxyamino groups wherein the aliphatic portion chain length is preferably as described above. The R substituents can also be substituted with other groups, such as halogens (e.g. chloride, fluoride, and bromide), halogenated aliphatic or aryl groups, and hydroxy (e.g. hydroxy substituted aliphatic groups). Suitable halogenated R groups could include, for example, tri-halogenated (preferably fluoro) alkyl groups such as -$R^1$-$C(F)_3$, wherein $R^1$ is $C_1$–$C_3$ alkyl. Examples of such polysiloxanes include polymethyl-3,3,3 trifluoropropylsiloxane.

Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred. Other suitable R groups include methyl, methoxy, ethoxy, propoxy, and aryloxy. The three R groups on the end caps of the silicone may also represent the same or different groups.

The nonvolatile polyalkylsiloxane fluids that may be used include, for example, polydimethylsiloxanes. These siloxanes are available, for example, from the General Electric Company in their Viscasil R and SF 96 series, and from Dow Coming in their Dow Corning 200 series.

The polyalkylaryl siloxane fluids that may be used, also include, for example, polymethylphenylsiloxanes. These siloxanes are available, for example, from the General Electric Company as SF 1075 methyl phenyl fluid or from Dow Corning as 556 Cosmetic Grade Fluid.

The polyether siloxane copolymers that may be used include, for example, a polypropylene oxide modified polydimethylsiloxane (e.g., Dow Corning DC-1248) although ethylene oxide or mixtures of ethylene oxide and propylene oxide may also be used. The ethylene oxide and polypropylene oxide level must be sufficiently low to prevent solubility in water and the composition hereof.

Suitable alkylamino substituted silicones include those conforming to the following formula:

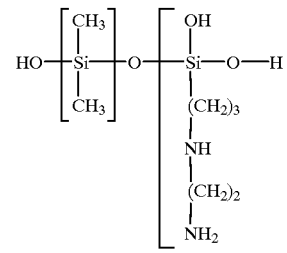

wherein x and y are integers. This polymer is also known as "amodimethicone".

Suitable cationic silicone fluids include those conforming to the formula described hereinabove, wherein $(R_1)_a G_{3-a}$—Si—$(-OSiG_2)_n$-$(-OSiG_b(R_1)_{2-b})_m$-O-$SiG_{3-a}(R_1)_a$ in which G is chosen from the group consisting of hydrogen, phenyl, OH, $C_1$–$C_8$ alkyl and preferably methyl; a denotes 0 or an integer from 1 to 3, and preferably equals 0; b denotes 0 or 1 and preferably equals 1; the sum n+m is a number from 1 to 2,000 and preferably from 50 to 150, n being able to denote a number from 0 to 1,999 and preferably from 49 to 149 and m being able to denote an integer from 1 to 2,000 and preferably from I to 10; $R_1$ is a monovalent radical of formula $CqH_{2q}L$ in which q is an integer from 2 to 8 and L is chosen from the groups

—$N(R_2)CH_2$—$CH_2$—$N(R_2)_2$

—$N(R_2)_2$

—$N(R_2)_3 A^-$

—$N(R_2)CH_2$—$CH_2$—$NR_2H_2 A^-$ in which $R_2$ is chosen from the group consisting of hydrogen, phenyl, benzyl, a saturated hydrocarbon radical, preferably an alkyl radical containing from 1 to 20 carbon atoms, and $A^-$ denotes a halide ion.

An especially preferred cationic silicone corresponding to the previous formula is the polymer known as "trirnethylsilylamodimethicone", which conforms to the following formula:

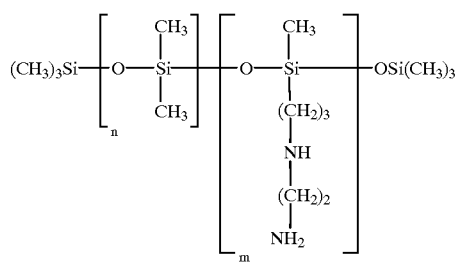

Other silicone cationic polymers which can be used in the shampoo compositions are those which conform to the following formula:

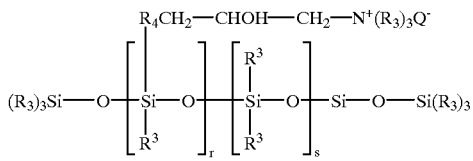

where $R^3$ denotes a monovalent hydrocarbon radical having from 1 to 18 carbon atoms, preferably an alkyl or alkenyl radical such as methyl; $R_4$ denotes a hydrocarbon radical, preferably a $C_1$–$C_{18}$ alkylene radical or a $C_1$–$C_{18}$, and more preferably $C_1$–$C_8$, alkyleneoxy radical; $Q^-$ is a halide ion, preferably chloride; r denotes an average statistical value from 2 to 20, preferably from 2 to 8; s denotes an average statistical value from 20 to 200, and preferably from 20 to 50. A preferred polymer of this class is available from Union Carbide under the name "UCAR SILICONE ALE 56."

Other suitable silicone fluids for use in the silicone conditioning agents are insoluble silicone gums. These gums are polyorganosiloxane materials having a viscosity at 25° C. of greater than or equal to 1,000,000 centistokes. Silicone gums are described in U.S. Pat. No. 4,152,416; Noll and Walter, *Chemistry and Technology of Silicones*, New York: Academic Press 1968; and in General Electric Silicone Rubber Product Data Sheets SE 30, SE 33, SE 54 and SE 76, all of which are incorporated herein by reference. The silicone gums will typically have a mass molecular weight in excess of about 200,000, generally between about 200,000 and about 1,000,000, specific examples of which include polydimethylsiloxane, (polydimethylsiloxane) (methylvinylsiloxane) copolymer, poly(dimethylsiloxane) (diphenyl siloxane)(methylvinylsiloxane) copolymer and mixtures thereof.

The silicone hair conditioning agent can also comprise a mixture of polydimethylsiloxane gum (viscosity greater than about 1,000,000 centistokes) and polydimethylsiloxane oil (viscosity from about 10 to about 100,000 centistokes), wherein the ratio of gum to fluid is from about 30:70 to about 70:30, preferably from about 40:60 to about 60:40.

Another category of nonvolatile, insoluble silicone fluid conditioning agents are high refractive index silicones, having a refractive index of at least about 1.46, preferably at least about 1.48, more preferably at least about 1.52, most preferably at least about 1.55. Although not intended to necessarily be limiting, the refractive index of the polysiloxane fluid will generally be less than about 1.70, typically less than about 1.60. Polysiloxane "fluid" includes oils as well as gums.

The high refractive index polysiloxane fluid suitable for purposes hereof includes those conforming to the formula described hereinabove, as well as cyclic polysiloxanes such as those conforming to the following formula:

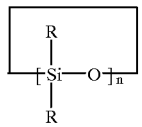

wherein R is as defined above, n is from about 3 to about 7, preferably from 3 to 5.

The high refractive index polysiloxane fluids contain a sufficient amount of aryl-containing R substituents to increase the refractive index to the desired level, which is described above. In addition, R and n must be selected so that the material is nonvolatile, as defined above.

Aryl-containing substituents contain alicyclic and heterocyclic five and six membered aryl rings, and substituents containing fused five or six membered rings. The aryl rings themselves can be substituted or unsubstituted. Substituents include aliphatic substituents, and can also include alkoxy substituents, acyl substituents, ketones, halogens (e.g., Cl and Br), amines, etc. Exemplary aryl-containing groups include substituted and unsubstituted arenes, such as phenyl, and phenyl derivatives such as phenyls with $C_1$–$C_5$ alkyl or alkenyl substituents, e.g., allylphenyl, methyl phenyl and ethyl phenyl, vinyl phenyls such as styrenyl, and phenyl alkynes (e.g. phenyl $C_{2-C4}$ alkynes). Heterocyclic aryl groups include substituents derived from furan, imidazole, pyrrole, pyridine, etc. Fused aryl ring substituents include, for example, napthalene, coumarin, and purine.

In general, the high refractive index polysiloxane fluids will have a degree of aryl-containing substituents of at least about 15%, preferably at least about 20%, more preferably at least about 25%, even more preferably at least about 35%, most preferably at least about 50%. Typically, although it is not intended to necessarily limit the invention, the degree of aryl substitution will be less than about 90%, more generally less than about 85%, preferably from about 55% to about 80%.

The polysiloxane fluids are also characterized by relatively high surface tensions as a result of their aryl substitution. In general, the polysiloxane fluids hereof will have a surface tension of at least about 24 dynes/cm², typically at least about 27 dynes/cm². Surface tension, for purposes hereof, is measured by a de Nouy ring tensiometer according to Dow Corning Corporate Test Method CTM 0461, Nov. 23, 1971. Changes in surface tension can be measured according to the above test method or according to ASTM Method D 1331.

Preferred high refractive index polysiloxane fluids have a combination of phenyl or phenyl derivative substituents (preferably phenyl), with alkyl substituents, preferably $C_1$–$C_4$ alkyl (most preferably methyl), hydroxy, $C_1$–$C_4$ alkylamino (especially —$R^1NHR^2$—$NH2$ where each $R^1$ and $R^2$ independently is a $C_1$–$C_3$ alkyl alkenyl, and/or alkoxy. High refractive index polysiloxanes are available from Dow Corning Corporation (Midland, Mich., U.S.A.) Huls America (Piscataway, N.J., U.S.A.), and General Electric Silicones (Waterford, N.Y., U.S.A.).

It is preferred to utilize high refractive index silicones in solution with a spreading agent, such as a silicone resin or a surfactant, to reduce the surface tension by a sufficient amount to enhance spreading and thereby enhance glossiness (subsequent to drying) of hair treated with the composition. In general, a sufficient amount of the spreading agent to reduce the surface tension of the high refractive index polysiloxane fluid by at least about 5%, preferably at least about 10%, more preferably at least about 15%, even more preferably at least about 20%, most preferably at least about 25%. Reductions in surface tension of the polysiloxane fluid/spreading agent mixture can provide improved shine enhancement of the hair.

Also, the spreading agent will preferably reduce the surface tension by at least about 2 dynes/cm², preferably at least about 3 dynes/cm², even more preferably at least about 4 dynes/cm², most preferably at least about 5 dynes/cm².

The surface tension of the mixture of the polysiloxane fluid and the spreading agent, at the proportions present in the final product, is preferably 30 dynes/cm² or less, more preferably about 28 dynes/cm² or less most preferably about 25 dynes/cm² or less. Typically the surface tension will be in the range of from about 15 to about 30, more typically from about 18 to about 28, and most generally from about 20 to about 25 dynes/cm².

The weight ratio of the highly aylated polysiloxane fluid to the spreading agent will, in general, be between about 1000:1 and about 1:1, preferably between about 100:1 and about 2:1, more preferably between about 50:1 and about 2:1, most preferably from about 25:1 to about 2:1. When fluorinated surfactants are used, particularly high polysiloxane: spreading agent ratios may be effective due to the efficiency of these surfactants. Thus it is contemplated that ratios significantly above 1000:1 may be used.

References disclosing examples of some suitable silicone fluids for use in the shampoo compositions include U.S. Pat. No. 2,826,551, U.S. Pat. No. 3,964,500, U.S. Pat. No. 4,364,837, British Patent 849,433, and *Silicon Compounds*, Petrarch Systems, Inc. (1984), all of which are incorporated herein by reference.

Silicone resins can be included in the silicone conditioning agent. These resins are highly crosslinked polymeric siloxane systems. The crosslinking is introduced through the incorporation of trifunctional and tetrafunctional silanes with monofunctional or difunctional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units (and hence, a sufficient level of crosslinking) such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0. Silanes used in the manufacture of silicone resins include monomethyl-, dimethyl-, trimnethyl-, monophenyl-, diphenyl-, methylphenyl-, monovinyl-, and methylvinyl-chlorosilanes, and tetrachlorosilane, with the methyl-substituted silanes being most commonly utilized. Preferred resins are offered by General Electric as GE SS4230 and SS4267. Commercially available silicone resins will generally be supplied in a dissolved form in a low viscosity volatile or nonvolatile silicone fluid. The silicone resins for use herein should be supplied and incorporated into the present compositions in such dissolved form, as will be readily apparent to those skilled in the art.

Background material on silicones including sections discussing silicone fluids, gums, and resins, as well as manufacture of silicones, can be found in Encyclopedia of Polymer Science and Engineering, Volume 15, Second Edition, pp 204–308, John Wiley & Sons, Inc., 1989, incorporated herein by reference.

Silicone materials and silicone resins in particular, can conveniently be identified according to a shorthand nomenclature system well known to those skilled in the art as "MDTQ" nomenclature. Under this system, the silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO1.5$; and Q' denotes the quadri- or tetra-functional unit $SiO_2$. Primes of the unit symbols, e.g., M', D', T', and Q' denote substituents other than methyl, and must be specifically defined for each occurrence. Typical alternate substituents include groups such as vinyl, phenyls, amines, hydroxyls, etc. The molar ratios of the various units, either in terms of subscripts to the symbols indicating the total number of each type of unit in the silicone (or an average thereof) or as specifically indicated ratios in combination with molecular weight complete the description of the silicone material under the MDTQ system. Higher relative molar amounts of T, Q, T' and/or Q' to D, D', M and/or M' in a silicone resin is indicative of higher levels of crosslinking. As discussed before, however, the overall level of crosslinking can also be indicated by the oxygen to silicon ratio.

The silicone resins for use herein which are preferred are MQ, MT, MTQ, MDT and MDTQ resins. Thus, the preferred silicone substituent is methyl. Especially preferred are MQ resins wherein the M:Q ratio is from about 0.5:1.0 to about 1.5:1.0 and the average molecular weight of the resin is from about 1000 to about 10,000.

The weight ratio of the nonvolatile silicone fluid, having refractive index below 1.46, to the silicone resin component, when used, is preferably from about 4:1 to about 400:1, preferably this ratio is from about 9:1 to about 200:1, more preferably from about 19:1 to about 100:1, particularly when the silicone fluid component is a polydimethylsiloxane fluid or a mixture of polydimethylsiloxane fluid and polydimethylsiloxane gum as described above. Insofar as the silicone resin forms a part of the same phase in the compositions hereof as the silicone fluid, i.e. the conditioning active, the sum of the fluid and resin should be included in determining the level of silicone conditioning agent in the composition.

Suspending Agents

The shampoo compositions of the present invention further comprises a suspending agent at concentrations effective for suspending the conditioning agents such as the preferred silicone conditioning agent, or other water-insoluble material, in dispersed form in the shampoo compositions. Without being limited by theory, applicants believe that these suspending agents provide suspension for the conditioning agents, especially those having a particle size above about 0.2 microns, preferably above about 1 micron and more preferably above about 2 microns and most preferably above about 5 microns.. Such concentrations range from about 0.1% to about 10%, preferably from about 0.3% to about 5.0%, by weight of the shampoo compositions.

Suspending agents include crystalline suspending agents which can be categorized as acyl derivatives, long chain amine oxides, and mixtures thereof, concentrations of which range from about 0.1% to about 5.0%, preferably from about 0.5% to about 3.0%, by weight of the shampoo compositions. These suspending agents are described in U.S. Patent 4,741,855, which description is incorporated herein by reference. These preferred suspending agents include ethylene glycol esters of fatty acids preferably having from about 16 to about 22 carbon atoms. More preferred are the ethylene glycol stearates, both mono and distearate, but particularly the distearate containing less than about 7% of the mono stearate. Other suitable suspending agents include alkanol amides of fatty acids, preferably having from about 16 to about 22 carbon atoms, more preferably about 16 to 18 carbon atoms, preferred examples of which include stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); glyceryl esters (e.g., glyceryl distearate) and long chain esters of long chain alkanol amides (e.g., stearamide diethanolamide distearate, stearamide monoethanolamide stearate). Long chain acyl derivatives, ethylene glycol esters of long chain carboxylic acids, long chain amine oxides, and alkanol amides of long chain carboxylic acids in addition to the preferred materials listed above may be used as suspending agents. For example, it is contemplated that suspending agents with long chain hydrocarbyls having $C_8$–$C_{22}$ chains may be used.

Other long chain acyl derivatives suitable for use as suspending agents include N,N-dihydrocarbyl amido benzoic acid and soluble salts thereof (e.g., Na, K), particularly N,N-di(hydrogenated) $C_{16}$, $C_{18}$ and tallow amido benzoic acid species of this family, which are commercially available from Stepan Company (Northfield, Ill., USA).

Examples of suitable long chain amine oxides for use as suspending agents include alkyl ($C_{16}$–$C_{22}$) dimethyl amine oxides, e.g., stearyl dimethyl amine oxide Other suitable suspending agents include xanthan gum at concentrations ranging from about 0.3% to about 3%, preferably from about 0.4% to about 1.2%, by weight of the shampoo compositions. The use of xanthan gum as a suspending agent in silicone containing shampoo compositions is described, for example, in U.S. Pat. No. 4,788,006, which description is incorporated herein by reference. Combinations of long chain acyl derivatives and xanthan gum may also be used as a suspending agent in the shampoo compositions. Such combinations are described in U.S. Pat. No. 4,704,272, which description is incorporated herein by reference.

Other suitable suspending agents include carboxyvinyl polymers. Preferred among these polymers are the copolymers of acrylic acid crosslinked with polyallylsucrose as described in U.S. Pat. No. 2,798,053, which description is incorporated herein by reference. Examples of these polymers include Carbopol 934, 940, 941, and 956, available from B. F. Goodrich Company.

Other suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow)amine. Still other suitable suspending agents include di(hydrogenated tallow)phthalic acid amide, and crosslinked maleic anhydride-methyl vinyl ether copolymer.

Other suitable suspending agents may be used in the shampoo compositions, including those that can impart a gel-like viscosity to the composition, such as water soluble or colloidally water soluble polymers like cellulose ethers (e.g., methylcellulose, hydroxybutyl methylcellulose, hyroxypropylcellulose, hydroxypropyl methylcellulose, hydroxyethyl ethylcellulose and hydroxyethylcellulose), guar gum, polyvinyl alcohol, polyvinyl pyrrolidone, hydroxypropyl guar gum, starch and starch derivatives, and other thickeners, viscosity modifiers, gelling agents, etc. Mixtures of these materials can also be used.

Deposition Polymer

A deposition polymer is an essential element of the present invention. Without being limited by theory, Applicants believe that the deposition polymer ensures deposition of the first conditioning agent having a mean particle range of less than about 2 microns. It will generally be present at levels of from 0.01 to 5%, preferably from about 0.05 to 1%, more preferably from about 0.08% to about 0.5% by weight The polymer may be a homopolymer or be formed from two or more types of monomers. The molecular weight of the polymer will generally be between about 5,000 and about 20,000,000, preferably between about 50,000 and about 5,000,000, and most preferably in the range between about 100,000 to about 2,000,000.

Preferably the deposition polymer is a cationic polymer and preferably will have cationic nitrogen containing groups, or a mixture thereof. The cationic charge density has been found to need to be at least about 0.1 meq/g, preferably above about 0.5 and most preferably above about 0.8 or higher. The cationic charge density should not exceed about 5 meq/g, it is preferably less than about 3 and more preferably less than about 2 meq/g. The charge density can be measured using the Kjeldahl method and should be within the above limits at the desired pH of use, which will in general be from about 3 to 9 and preferably between 4 and 8.

The cationic nitrogen-containing group will generally be present as a substituent on a fraction of the total monomer units of the cationic polymer. Thus when the cationic polymer is not a homopolymer it can contain spacer non-cationic monomer units. Such polymers are described in the CTFA Cosmetic Ingredient Directory, 3rd edition.

Suitable cationic polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1–C7 alkyl groups, more preferably C1–C3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the shampoo. In general secondary and tertiary amines, especially tertiary, are preferred.

Amines substituted vinyl monomers and amines can be polymerized in the amine form and then converted to ammonium by quaternization.

Suitable cationic amino and quaternary ammonium monomers include, for example, vinyl compounds substituted with dialkyl aminoalkyl acrylate, dialkylamino alkylmethacrylate, monoalkylaminoalkyl acrylate, monoalkylaminoalkyl methacrylate, trialkyl methacryloxyalkyl ammonium salt, trialkyl acryloxyalkyl ammonium sale, diallyl quaternary ammonium salts, and vinyl quaternary ammonium monomers having cyclic cationic nitrogen-containing rings such as pyridinium, imidazolium, and quaternized pyrrolidine, e.g., alkyl vinyl imidazolium, and quaternized pyrrolidine, e.g., alkyl vinyl imidazolium, allyl vinyl pyridinium, alkyl vinyl pyrrolidine salts. The alkyl portions of these monomers are preferably lower alkyls such as the $C_1$–$C_3$ alkyls, more preferably $C_1$ and $C_2$ alkyls.

Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably $C_1$–$C_7$ hydrocarbyls, more preferably $C_1$–$C_3$ alkyls.

The cationic polymers hereof can comprise mixtures of monomer units derived from amine- and/or quaternary ammonium-substituted monomer and/or compatible spacer monomers.

Suitable cationic hair conditioning polymers include, for example: copolymers of 1-vinyl-2-pyrrolidine and 1-vinyl-3-methyl-imidazolium salt (e.g., Chloride salt) (referred to in the industry by the Cosmetic, Toiletry, and Fragrance Association, "CTFA" as Polyquaternium-16) such as those commercially available from BASF Wyandotte Corp. (Parsippany, N.J., USA) under the LUVIQUAT tradename (e.g., LUVIQUAT FC 370); copolymers of 1-vinyl-2-pyrrolidine and dimethylaminoethyl methacrylate (referred to in the industry by CTFA and Polyquaternium-11) such as those commercially from ISP Corporation (Wayne, N.J., USA) under the GAFQUAT tradename (e.g., GAFQAT 755N); cationic diallyl quaternary ammonium-containing polymers including, for example, dimethyldiallyammonium chloride homopolymer and copolymers of acrylamide and dimethyldiallyammonium chloride, referred to in the industry (CTFA) as Polyquatemium 6 and Polyquatemium 7, respectively; and mineral acid salts of amino-alkyl esters of homo-and co-polymers of unsaturated carboxylic acids having from 3 to 5 carbon atoms, as described in U.S. Pat. No. 4,009,256, incorporated herein by reference.

Other cationic polymers that can be used include polysaccharide polymers, such as cationic cellulose derivatives and cationic starch derivatives. Cationic polysaccharide polymer materials suitable for use herein include those of the formula:

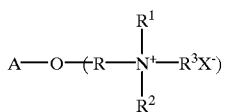

wherein: A is an anhydroglucose residual group, such as starch or cellulose anhydroglucose residual, R is an alkylene oxyalklene, polyoxyalkylene, or hydroxyalkylene group, or combination thereof, $R^1$, $R^2$ and $R^3$ independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in $R^1$, $R^2$ and $R^3$) preferably being about 20 or less, and X is an anionic counterion, as previously described.

Cationic cellulose is available from Amerchol Corp. (Edison, N.J., USA) in their Polymer JR (trademark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

Other cationic polymers that can be used include cationic guar gum derivatives, such as guar hydroxypropyltrimonium chloride (commercially available from Celanese Corp. in their Jaguar trade mark series). Other materials include quaternary nitrogen-containing cellulose ethers (e.g., as described in U.S. Pat. No. 3,962,418, incorporated by reference herein), and copolymers of etherified cellulose and starch (e.g., as described in U.S. Pat. No. 3,958,581, incorporated by reference herein).

The deposition polymer does not have to be soluble in the shampoo composition. Preferably, however, the cationic polymer is either soluble in the shampoo composition, or in a complex coacervate phase in the shampoo composition formed by the cationic polymer and anionic material. Complex coacervates of the cationic polymer can be formed with anionic surfactants or with anionic polymers that can optionally be added to the composition hereof (e.g., sodium polystyrene sulfonate).

Coacervate formation is dependent upon a variety of criteria such as molecular weight, concentration, and ratio of interacting ionic materials, ionic strength (including modification of ionic strength, for example, by addition of salts), charge density of the cationic and anionic species, pH, and temperature. Coacervate systems and the effect of these parameters have been described, for example, by J. Caelles, et al., "Anionic and Cationic Compounds in Mixed Systems", *Cosmetics & Toiletries*, Vol. 106, April 1991, pp 49–54, C. J. van Oss, "Coacervation, Complex-Coacervation and Flocculation", *J. Dispersion Science and Technology*, Vol. 9 (5, 6), 1988–89, pp 561–573, and D. J. Burgess, "Practical Analysis of Complex Coacervate Systems", *J. of Colloid and Interface Science*, Vol. 140, No. 1, November 1990, pp 227–238, which descriptions are incorporated herein by reference.

It is believe to be particularly advantageous for the cationic polymer to be present in the shampoo in a coacervate phase, or to form a coacervate phase upon application or rinsing of the shampoo to or from the hair. Complex coacervates are believed to more readily deposit on the hair. Thus, in general, it is preferred that the cationic polymer exist in the shampoo as a coacervate phase or form a coacervate phase upon dilution. If not already a coacervate in the shampoo, the cationic polymer will preferably exist in a complex coacervate form in the shampoo upon dilution with water to a water:shampoo composition rate ratio of about 20:1, more preferably at about 10:1, even more preferably at about 8:1.

Techniques for analysis of formation of complex coacervates are known in the art. For example, microscopic analyses of the shampoo compositions, at any chosen stage of dilution, can be utilized to identify whether a coacervate phase has formed. Such coacervate phase will be identifiable as an additional emulsified phase in the composition. The use of dyes can aid in distinguishing the coacervate phase from other insoluble phase dispersed in the composition.

Preferably the deposition polymer is selected from the group comprising hydroxyalkyl cellulose ethers and cationic guar derivatives. Particularly preferred deposition polymers are Jaguar C13S, Jaguar C15, Jaguar C17 and Jaguar C16 and Jaguar C162. Preferred cellulose ethers include Polymer JR400, JR30M and JR 125.

Water

The shampoo compositions of the present invention comprise from about 20% to about 94%, preferably from about 50% to about 94%, more preferably from about 60% to about 85%, by weight of water.

Other Optional Components

The shampoo compositions of the present invention may further comprise one or more optional components known for use in shampoo or conditioning compositions, provided that the optional components are physically and chemically compatible with the essential component described herein, or do not otherwise unduly impair product stability, aesthetics or performance. Concentrations of such optional components typically range from about 0.001% to about 10% by weight of the shampoo compositions.

Optional components include anti static agents, dyes, organic solvents or diluents, pearlescent aids, foam boosters, additional surfactants or cosurfactants (nonionic, cationic, zwitterionic), pediculocides, pH adjusting agents, perfumes, preservatives, proteins, skin active agents, suspending agents, styling polymers, sunscreens, thickeners, vitamins, and viscosity adjusting agents. This list of optional components is not meant to be exclusive, and other optional components can be used.

Method of Manufacture

The shampoo compositions of the present invention can be prepared by using various formulation and mixing techniques or methods known in the art for preparing surfactant or conditioning compositions, or other similar compositions.

Method of Use

The shampoo compositions of the present invention are used in a conventional manner for cleansing and conditioning hair or skin. An effective amount of the composition for cleansing and conditioning the hair or skin is applied to the hair or skin, that has preferably been wetted with water, and then rinsed off. Such effective amounts generally range from about 1 g to about 50 g, preferably from about 1 g to about 20 g. Application to the hair typically includes working the composition through the hair such that most or all of the hair is contacted with the composition.

This method for cleansing and conditioning the hair comprises the steps of: a) wetting the hair with water, b) applying an effective amount of the shampoo composition to the hair, and c) rinsing the shampoo composition from the hair using water. These steps can be repeated as many times as desired to achieve the desired cleansing and conditioning benefit.

EXAMPLES

The shampoo compositions illustrated in Examples I–XV illustrate specific embodiments of the shampoo compositions of the present invention, but are not intended to be limiting thereof. Other modifications can be undertaken by the skilled artisan without departing from the spirit and scope of this invention. These exemplified embodiments of the shampoo compositions of the present invention provide cleansing of hair and improved hair conditioning performance.

The compositions are prepared as follows.

The large particle silicone emulsion is prepared by adding about 70% Dimethicone, 29% Ammonium Laureth-3 Sulfate (solution basis, 25 wt. % active) and 1% Sodium Chloride, the percentages being on a weight basis of the silicone premix, to a high shear mixing vessel and mixing for about 30 minutes or until the desired silicone particle size is achieved (typically the mean particle size is from about 15 microns to about 100 microns).

For Examples I–XV, about one-third to all of the total alkyl sulfate surfactant (ammonium laureth-3 sulfate (added as a 25% solution) and/or ammonium lauryl sulfate (added as a 25% solution)) is added to a jacketed mix tank and heated to about 74° C. with slow agitation to form a surfactant solution. Cocamide MEA and fatty alcohol, as applicable, are added to the tank and allowed to disperse. Ethylene glycol distearate (EGDS) is then added to the mixing vessel, and melted. After the EGDS is well dispersed (usually about 5 to 20 minutes) polyethylene glycol and the preservative, if used are added and mixed into the surfactant solution. This mixture is passed through a heat exchanger where it is cooled to about 35° C. and collected in a finishing tank. As a result of this cooling step, the ethylene glycol distearate crystallizes to form a crystalline network in the product. The remainder of the ammonium laureth sulfate, lauryl sulfate and other ingredients including the silicone emulsions are added to the finishing tank with ample agitation to insure a homogeneous mixture. A sufficient amount of the silicone emulsions are added to provide the desired level of dimethicone in the final product. The non-silicone polymers are typically dispersed in water as a 1% to 10% solution before addition to the final mix. Once all ingredients have been added, ammonium xylene sulfonate or additional sodium chloride can be added to the mixture to thin or thicken respectively to achieve a desired product viscosity. Preferred viscosities range from about 3500 to about 9000 cS at 25° C. (as measured by a Wells-Brookfield cone and plate viscometer at 15/s).

The compositions of the Examples can provide excellent in-use hair cleaning, lather, mildness, dandruff control (where applicable), and especially conditioning and conditioning impression.

| Component | Example Number | | | | |
| --- | --- | --- | --- | --- | --- |
| | I | II | III | IV | V |
| Ammonium Laurel Sulfate | 4 | 6 | 4 | 5 | 4 |
| Ammonium Laureth-3 Sulfate | 12 | 10 | 12 | 15 | 12 |
| Cocamidopropylbetaine | 0 | 0 | 2.5 | 0 | 1 |
| Jaguar C17 (5) | 0.15 | 0.15 | 0.05 | 0.30 | 0.15 |
| Cocamide MEA | 0.80 | 0.80 | 0.80 | 0.80 | 0 |
| Cetyl Alcohol | 0.42 | 0.42 | 0.42 | 0.42 | 0.42 |
| Stearyl Alcohol | 0.18 | 0.18 | 0.18 | 0.18 | 0.18 |
| Ethylene Glycol Distearate | 1.50 | 1.50 | 1.50 | 1.50 | 1.50 |
| Dimethicone (1) | 1.00 | 3.00 | 1.00 | 1.00 | 1.00 |
| Dimethicone (4) | 2 | 1 | 1 | 1.5 | 1.25 |
| Perfume Solution | 0.70 | 0.70 | 0.70 | 0.70 | 0.70 |
| DMDM Hydantoin | 0.37 | 0.37 | 0.37 | 0.37 | 0.37 |
| Color Solution (ppm) | 64 | 64 | 64 | 64 | 64 |
| Water and Minors | q.s. to 100% | | | | |

| | VI | VII | VIII | IX | X |
| --- | --- | --- | --- | --- | --- |
| Ammonium Laureth-3 Sulfate | 14.00 | 11.75 | 14.0 | 14.85 | 12.50 |
| Cocamidopropylbetaine | 2.70 | 2.25 | 2.70 | 1.85 | 4.20 |
| Polyquaternium-10 (3) | 0.15 | 0.13 | 0.15 | 0.15 | 0.15 |
| Cocamide MEA | 0.80 | 0.80 | 0.80 | 0.80 | 0 |
| Cetyl Alcohol | 0 | 0.42 | 0.42 | 0.42 | 0.42 |
| Stearyl Alcohol | 0 | 0.18 | 0.18 | 0.18 | 0.18 |
| Ethylene Glycol Distearate | 1.50 | 1.50 | 1.50 | 1.50 | 1.50 |
| Dimethicone (1) | 1.00 | 2.00 | 1.00 | 1.00 | 1.00 |
| Dimethicone (4) | 1.5 | 1.0 | 1.0 | 2.0 | 2.25 |
| Perfume Solution | 0.70 | 0.70 | 0.70 | 0.70 | 0.70 |
| DMDM Hydantoin | 0.37 | 0.37 | 0.37 | 0.37 | 0.37 |
| Color Solution (ppm) | 64 | 64 | 64 | 64 | 64 |
| Water and Minors | q.s. to 100% | | | | |

| | XI | XII | XIII | XIV | XV |
| --- | --- | --- | --- | --- | --- |
| Ammonium Laureth-3 Sulfate | 14.00 | 14.00 | 14.00 | 10.00 | 10.00 |
| Cocamidopropylbetaine | 2.70 | 2.70 | 2.70 | 2.00 | 2.00 |
| Polyquaternium-10 (6) | 0.15 | 0.15 | 0.15 | 0.10 | 0.10 |
| Cocamide MEA | 0.80 | 0.80 | 0 | 0.80 | 0.60 |
| Cetyl Alcohol | 0 | 0.42 | 0 | 0.42 | 0 |
| Stearyl Alcohol | 0 | 0.18 | 0 | 0.18 | 0 |
| Ethylene Glycol Distearate | 0 | 0 | 0 | 1.50 | 1.50 |
| Carbopol 981 (2) | 0.50 | 0.50 | 0.50 | 0 | 0 |
| Dimethicone (1) | 1.00 | 1.00 | 1.00 | 1.00 | 0.50 |
| Dimethicone (4) | 0.5 | 2.2 | 1.75 | 1.0 | 3.0 |
| Perfume Solution | 0.70 | 0.70 | 0.70 | 0.70 | 0.70 |
| DMDM Hydantoin | 0.37 | 0.37 | 0.37 | 0.37 | 0.37 |
| Color Solution (ppm) | 64 | 64 | 64 | 64 | 64 |
| Water and Minors | q.s. to 100% | | | | |

(1) Dimethicone is an emulsion of 60,000 csk polydimethyl siloxane with particle size of approximately 300 nm available from Dow Corning (DC 1664).
(2) Carbopol 981 is a crosslinked polyacrylate available from B.F. Goodrich.
(3) Polyquaternium-10 is JR30M, a cationic cellulose derived polymer available from Amerchol.
(4) A 40 (gum)/60 (fluid) weight ratio blend of SE-76 dimethicone gum available from General Electric Silicones Division and a dimethicone fluid having a viscosity of 350 centistokes.
(5) Jaguar C17 is a cationic polymer available from Rhone-Poulenc

| Component | Example Number |
|---|---|

(6) Polyquaternium-10 is JR400, a cationic cellulose derived polymer available from Amerchol.

What is claimed is:

1. An aqueous shampoo composition comprising:
   a) from about 5.0% to about 50% of an alkyl ether sulfate surfactant component confotmin& to the formula:

RO(CH$_2$H$_4$O)$_x$SO$_3$M wherein R is a C$_8$ to C$_{30}$ alkyl, x is 1 to 10, and M is selected from the group consisting of hydrgen, cation, monovalent metal cation, and polyvalent metal cation;
   b) from about 0.005% to about 10% of a conditioning component comprising:
      i) a first non-volatile conditioning agent having a mean particle size of less than about 2 microns; and
      ii) a second non-volatile conditioning agent having a mean particle size from about 5 microns to about 500 microns;
      iii) wherein sa first non-volatile conditioner agent and said second non-volatile conditioning agent are independently either polyalkyl or polyaryl siloxanes conforming to the formula;

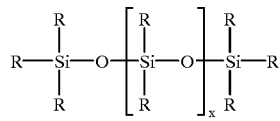

wherein R is aliphatic and is substituted or unsubsituted, and x is an integer from 1 to about 8,000;
   c) from about 0.01% to about 3.0% of a deposition polymer;
   d) from about 0.1% to about 5% of a suspending agent; and
   e) an aqueous carrier.

2. An aqueous shampoo composition according to claim 1 which comprises from about 8.0% to about 30% of said surfactant component and wherein said first non-volatile conditioning agent has a mean particle size of less than about 1 micron.

3. An aqueous shampoo composition according to claim 2 wherein said first non-volatile conditioning agent has a mean particle size range of from about 0.01 to about 0.5 microns and wherein said second non-volatile conditioning agent has a mean particle size range of from about 10 microns to about 200 microns.

4. An aqueous shampoo composition according to claim 3 wherein said first non-volatile conditioning agent has a mean particle size range of from about 0.01 to about 0.15 microns and wherein said second non-volatile conditioning agent has a mean particle size range of from about 15 microns to about 100 microns.

5. An aqueous shampoo composition according to claim 3 wherein the ratio of said first conditioning agent to said second conditioning agent is from about 1 to 10 to about 10 to 1.

6. An aqueous shampoo composition according to claim 5 wherein said non-volatile silicone conditioning agent is polydimethylsiloxane.

7. An aqueous shampoo composition according to claim 6 wherein said suspending agent is selected from the group consisting of long chain acyl derivatives having from 16 to 22 carbon atoms, long chain amines and amine oxides having from 16 to 22 carbon atoms.

8. An aqueous shampoo composition according to claim 7 wherein said suspending agent is a ethylene glycol ester of a fatty acid having from 16 to 22 carbon atoms.

9. An aqueous shampoo composition according to claim 8 wherein said surfactant component comprises: i) an ethoxylated alkyl sulfate surfactant having from about 1 to about 8 moles of ethoxylation; and ii) an amphoteric surfactant wherein said composition comprises less than about 5% of ethoxylated alkyl sulfate surfactant having less than 1 mole of ethoxylation and wherein said deposition polymer is a cationic cellulosic polymer hair conditioning agent has a cationic charge density of from about 0.7 meq/gram.

10. An aqueous shampoo composition according to claim 9 wherein said composition comprises an additional anionic surfactant and wherein said composition comprises less than about 2% of ethoxylated surfactant having less than 1 mole of ethoxylation.

11. An aqueous shampoo composition according to claim 10 wherein said cationic cellulosic polymer hair conditioning agent is Polyquatemium-10.

12. An aqueous shampoo composition according to claim 11 wherein said cationic cellulosic polymer hair conditioning agent has a cationic charge density of from about 0.9 meq/gram to about 1.5 meq/gram.

13. An aqueous shampoo composition according to claim 12 wherein said amphoteric surfactant is cocoamidopropyl betaine and comprises from about 1% to about 10% of the composition.

14. An aqueous shampoo composition according to claim 13 wherein said amphoteric surfactant is cocoamidopropyl betaine and comprises from about 2% to about 5% of the composition.

15. An aqueous shampoo composition according to claim 14 wherein said non-volatile silicone conditioning agent comprises from about 0.05% to about 4% of the composition.

16. An aqueous shampoo composition according to claim 15 wherein non-volatile said silicone conditioning agent comprises from about 0.2% to about 3% of the composition.

17. An aqueous shampoo composition according to claim 1, further comprising from about 0.0001% to about 5% of an anti-dandruffagent.

18. A method for cleansing and conditioning hair, comprising the steps of: (a) wetting hair with water, (b) applying an effective amount of a shampoo composition, according to claim 1 to the hair, and (c) rinsing said shampoo composition from said hair using water.

19. An aqueous shampoo composition according to claim 1, wherein said conditioning component has a viscosity, measured at about 25° C., from about 20 centistokes to about 2,000,000 centistokes.

20. An aqueous shampoo composition according to claim 19, wherein said conditioning component has a viscosity, measured at about 25° C., from about 1000 centistokes to about 1,800,000 centistokes.

21. An aqueous shampoo composition according to claim 20, wherein said conditioning component has a viscosity, measured at about 25° C., from about 10,000 centistokes to about 1,500,000 centistokes.

22. An aqueous shampoo composition according to claim 21, wherein said conditioning component has a viscosity, measured at about 25° C., from about 30,000 centistokes to about 1,000,000 centistokes.

* * * * *